United States Patent [19]
Bruce et al.

[11] Patent Number: 5,804,694
[45] Date of Patent: Sep. 8, 1998

[54] COMMERCIAL PRODUCTION OF β-GLUCURONIDASE IN PLANTS

[75] Inventors: Wesley B. Bruce, Urbandale; Elizabeth Hood, Clive; David J. Peterson; James C. Register, III, both of Ames; Derrick Witcher, Urbandale; John A. Howard, West Des Moines, all of Iowa

[73] Assignee: ProdiGene, Inc., College Station, Tex.

[21] Appl. No.: 554,169

[22] Filed: Nov. 6, 1995

[51] Int. Cl.$^6$ ............ C12N 15/29; C12N 15/82; A01H 4/00; A01H 5/00
[52] U.S. Cl. ............ 800/205; 800/200; 800/230; 800/550; 435/59.1; 435/172.3; 435/320.1; 538/23.7; 538/24.1
[58] Field of Search ............ 800/205, 230, 800/250, DIG. 56; 536/24.1, 23.7, 23.2; 435/172.3, 69.1

[56] References Cited

U.S. PATENT DOCUMENTS

| | | | |
|---|---|---|---|
| 4,914,025 | 4/1990 | Manoil et al. | 435/69.8 |
| 5,460,952 | 10/1995 | Yu et al. | 435/69.1 |

FOREIGN PATENT DOCUMENTS

| | | |
|---|---|---|
| 0 342 926 | 11/1989 | European Pat. Off. . |
| WO 89/03887 | 5/1989 | WIPO . |
| WO 92/01042 | 1/1992 | WIPO . |
| WO 96/21029 | 7/1996 | WIPO . |

OTHER PUBLICATIONS

Jefferson et al. The EMBO Journal vol. 6 No. 13 pp. 3901–3907 GUS Fusions: B–Glucuronidase as a Sensitive and Versatile Gen Fusion, 1987.

Murray et al. Nucleic Acids Research. vol. 17 No. 2 Codon Usage in Plant Genes, 1989.

Cormejo et al. Plant Molecular Biology 23: 567–581, 1993 Activity of a Maize Ubiquitin Promoter in Transgenic Rice, 1993.

Terada et al., "Expression of CaMV35S–GUS Gene in Transgenic Rice Plants", Mol. Gen. Genet., vol. 220:389–392, (1990).

Praendl et al., "Development Regulation And Tissue–Specific Difference of Heat Shock Gene Expression In Transgenic Tobacco And Arabidopsis Plants", *Plant Molecular Biology*, vol. 28:73–82, (1995).

Hoeven et al., "Variability Of Organ–Specific Gene Expression In Transgenic Tobacco Plants", *Transgenic Research*, vol. 3:159–165, (1994).

Jefferson et al., "GUS Fusions: β–glucuronidase As A Sensitive And Versatile Gene Fusion Marker In Higher Plants", *The EMBo Journal*, vol. 6, No. 13, pp. 3901–3907, (1987).

Klein et al., "Factors Influencing Gene Delivery Into Zea Mays Cells By High–Velocity Microprojectiles", *Bio/Technology*, vol. 6:559–563, (1988).

Bruce et al., "Photoregulation Of A Phytochrome Gene Promoter From Oat Transferred Into Rice By Particle Bombardment", *Proc. Natl. Acad. Sci. USA*, vol. 86:9692–9696, (1989).

"Two Barley a–Amylase Gene . . . ", *J. Biological Chemistry*, 260(6):3731–3738 (1985).

"Comparison of Different Constitutive and Inducible Promoters . . . ", *Plant Molecular Biology*, 29: 637–646.

"Plant Seed Oil–bodies . . . ", *Bio/technology*, 13: 72–77 (Jan. 1997).

"Differences in Cell Type–Specific . . . ", *Med Gen Genet* 244: 391–400 (1994).

"Commercial Production of GUS From Transgenic Maize Seed . . . ", *In Vitro* 33(3): (1997), Abstract.

*Primary Examiner*—Douglas W. Robinson
*Assistant Examiner*—Thomas Haas
*Attorney, Agent, or Firm*—Foley & Lardner

[57] ABSTRACT

A method for commercial production of GUS entails heterologous expression of the protein in plants, in native conformation, at an expression level such that avidin represents at least 0.1% of total extracted protein. A genetic map of the integration locus allows for the identification of the GUS-expressing plant. Genetic loci on a plant chromosome are revealed that support high levels of GUS expression and that can be used as a site of integration for high level expression of other genes of interest.

20 Claims, 1 Drawing Sheet

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( x i ) SEQUENCE DESCRIPTION: SEQ ID NO:1:

Met  Leu  Arg  Pro  Val  Glu  Thr  Pro
1                   5

( 2 ) INFORMATION FOR SEQ ID NO:2:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( x i ) SEQUENCE DESCRIPTION: SEQ ID NO:2:

Val  Arg  Pro  Val  Glu  Thr  Pro
1                   5

COMMERCIAL PRODUCTION OF β-GLUCURONIDASE IN PLANTS

BACKGROUND OF THE INVENTION

Among the most commonly used reporter gene in plant molecular biology is that coding for β-glucuronidase. As an enzyme, GUS can act on a variety of substrates, some of which are commercially available, such as indole-β-glucuronide and methyl-umbelliferone β-glucuronide. The popularity of GUS is in part due to its versatility in that the expression of the enzyme can be determined by both cytochemical and spectrophotometric assays. The spectrophotometric assay is particularly sensitive; with methyl-umbelliferone β-glucuronide, fluorometric detection is feasible for picomoles of reaction product.

In plant research, GUS has been used as a marker for transformations, for the development and optimization of transformation protocols, as a reporter for identification of promoters, for determining tissue/developmental stage specificity of isolated promoters and genes, and for investigation of gene regulation agents. See, for example, Terada and Shimamoto *Molec. Gen. Genet.* 220: 389–92 (1990); Takahashi et al., *Plant J.* 2: 751–61 (1992); Matzke et al., *Plant Mol. Biol.* 22: 553–54 (1993); Webb et al., *Transgenic Res.* 3: 232–40 (1994); and Vandermaas et al., *Plant Mol. Biol.* 24: 401–05 (1994). Yet another common use for purified GUS is as a standard for enzyme assays in molecular biology protocols.

Purified enzyme is available from other sources, but commercial preparations are usually derived and purified from *E. coli*. Indeed, the *E. coli* derived uidA gene was the originally employed gus gene for all applications as described above. Later, the gene was optimized for plant work by introduction of a plant intron and changes at the 5'-end in the region of the initiation codon. See Van Der Hoeven et al., *Transgenic Res.* 3: 159–66 (1994); Schledzewski & Mendel, loc. cit. 3: 249–55 (1994); Vogeli-Lange et al., *Plant Molec. Biol.* 25: 299–311 (1994); Olsen et al., *J. Cell. Biochem.,* Suppl. 18A: 99 (1994); Praendl et al., *Plant Molec. Biol.* 28: 73–82 (1995); Aronen et al., *Canadian J. Forest Res.* 24: 2006–11 (1994); Vancanneyt et al., *Mol. Gen. Genet.* 220: 245 (1990); Ohta et al., Plant Cell Physiol. 31: 805 (1990); and Kato et al., *Plant Mol. Biol.* 9: 333 (1991).

Expression of foreign genes in plants is amply documented. In general, the expression of the foreign gene has been desired to benefit the plant, for example, by the action of expressed antifungals or growth factors; to improve an agronomic trait, such as fruit ripening or nutritional content; or to induce sterility in the context of creating hybrid plants. It also is feasible to express in plants heterologous genes, expressing high value products. In many cases, expression in plants could be the system of choice, because of such inherent advantages such as cost relative to that of tissue culture, and the concern about correct glycosylation and other post-translational processing of the expression product from other expression systems.

The level of protein expression in plants can be influenced by many factors. One factor is the choice of transcriptional promoters used. Recently, the range of available plant compatible promoters has increased to include tissue specific and inducible promoters. Some of the better documented constitutive promoters include the CaMV 35S promoter and tandem arrangements of this promoter, and the ubiquitin promoter. See Kay et al., *Science* 236: 1299 (1987), and European patent application No. 0 342 926. Yet other factors that can be manipulated to control levels of expression are the presence of transcriptional modification factors such as introns, polyadenylation and transcription termination sites. At the translational level, other factors to consider are the ribosomal binding site and the codon bias of the gene. High level expression of a gene product which then accumulates in the cytoplasm may result in toxicity to the plant cell; removal of the gene product from the cytoplasm thus may result in overall higher expression levels. Furthermore, intron sequences within the gus gene may also increase its expression level by stabilizing the transcript and allowing its effective translocation out of the nucleus. Most plant genes contain intron sequences. Among the known such intron sequences are the introns of the plant ubiquitin gene. See Callis et al., *Genes and Development,* 1: 1183–1200 (1987) and Cornejo et al. *Plant Mol. Biol.* 23: 567–581 (1993). Furthermore, it has been observed that the same construct inserted at different loci on the genome can vary in the level of expression in plants. The effect is believed to be due at least in part to the position of the gene on the chromosome, i.e., individual isolates will have different expression levels. See, for example, Hoever et al., *Transgenic Res.* 3: 159–66 (1994) (report regarding constructs containing gus or nptII). Yet another consideration in expression of foreign genes in plants is the level of stability of the transgenic genome, i.e., the tendency of a foreign gene to segregate from the population. If a selective marker is linked to the gene of interest, then selection can be applied to maintain the transgenic plant.

SUMMARY OF THE INVENTION

It is therefore an object of the present invention to provide a transgenic plant expressing GUS, that will allow commercial production of GUS at a significant savings over conventional methodology.

It also is an object of the resent invention to allow for tracking of unauthorized propagation of a plant by reference to a genetic map of the region where a heterozygotic gus gene has been introduced.

It is a further object of the present invention to provide an approach to cloning of a gene for high-level, heterologous expression, based on integration of the gene at a position analogous to that of a gus gene in a high-expressing, transgenic plant.

In accomplishing these and other objectives, there has been provided, in accordance with one aspect of the present invention, a transgenic plant that contains a DNA molecule comprised of a heterologous nucleotide sequence coding for GUS, wherein said nucleotide sequence is operably linked to a promoter to effect expression of GUS such that at least 0.1% of total extracted protein is GUS. In a preferred embodiment the DNA molecule incorporates plant-preferred codons. In another preferred embodiment the DNA molecule further comprises an intron sequence or a peptide export signal sequence which modifies expression of said heterologous nucleotide sequence. In yet another preferred embodiment the intron sequence is a plant ubiquitin intron sequence. In still another preferred embodiment the peptide export signal sequence is a barley alpha amylase peptide export signal sequence. In a further preferred embodiment the transgenic plant is a corn plant. In a yet further preferred embodiment the transgenic plant is of strain 106155 or strain 106202, germ plasm of which strains has been deposited under ATCC Accession Nos. 97330 and 97329, respectively.

In accordance with a second aspect of the present invention, there has been provided a method of producing GUS in commercial quantities, comprising the steps of (i) providing biomass from a plurality of plants, of which at least certain plants contain a DNA molecule comprised of a heterologous nucleotide sequence coding for GUS, wherein said nucleotide sequence is operably linked to a promoter to effect expression of GUS by those plants; and (ii) extracting GUS from the biomass. In a preferred embodiment the biomass is comprised of seeds.

In accordance with a third aspect of the present invention, there has been provided a method of determining whether a first transgenic plant of unknown parentage is derived from a second transgenic plant comprising the steps of:

(a) making a genetic map of the integration region of said nucleotide sequence coding for GUS in the second transgenic plant;

(b) making a genetic map of the integration region of the nucleotide sequence coding for GUS in the first transgenic plant; and then (c) comparing the maps of steps (a) and (b) to ascertain whether the insertion sites are the same.

In accordance with a fourth aspect of the present invention, there has been provided a method of expressing genes at high levels in a plant, comprising the steps of:

(a) cloning from a transgenic plant that expresses high levels of GUS a chromosomal fragment comprising a heterologous DNA sequence coding for GUS;

(b) cloning a chromosomal fragment corresponding to the chromosomal fragment of step (a) from a plant that does not express heterologous GUS;

(c) constructing an expression vector comprising the chromosomal fragment isolated in step (b);

(d) preparing a construct of a gene desired to be expressed at high levels within the vector, wherein the gene is located within plant chromosomal fragment of the vector of step (c) at a position corresponding to the heterologous gus gene;

(e) transforming the constructs into plant cells or tissue;

(f) propagating plants from the transformed cells or tissue; and (g) based on an assesment of expression level for the gene desired to be expressed at high levels, selecting at least one plant for further propagation to produce the gene product.

DETAILED DESCRIPTION OF THE PREFERRED EMBODIMENTS

Figure 1:
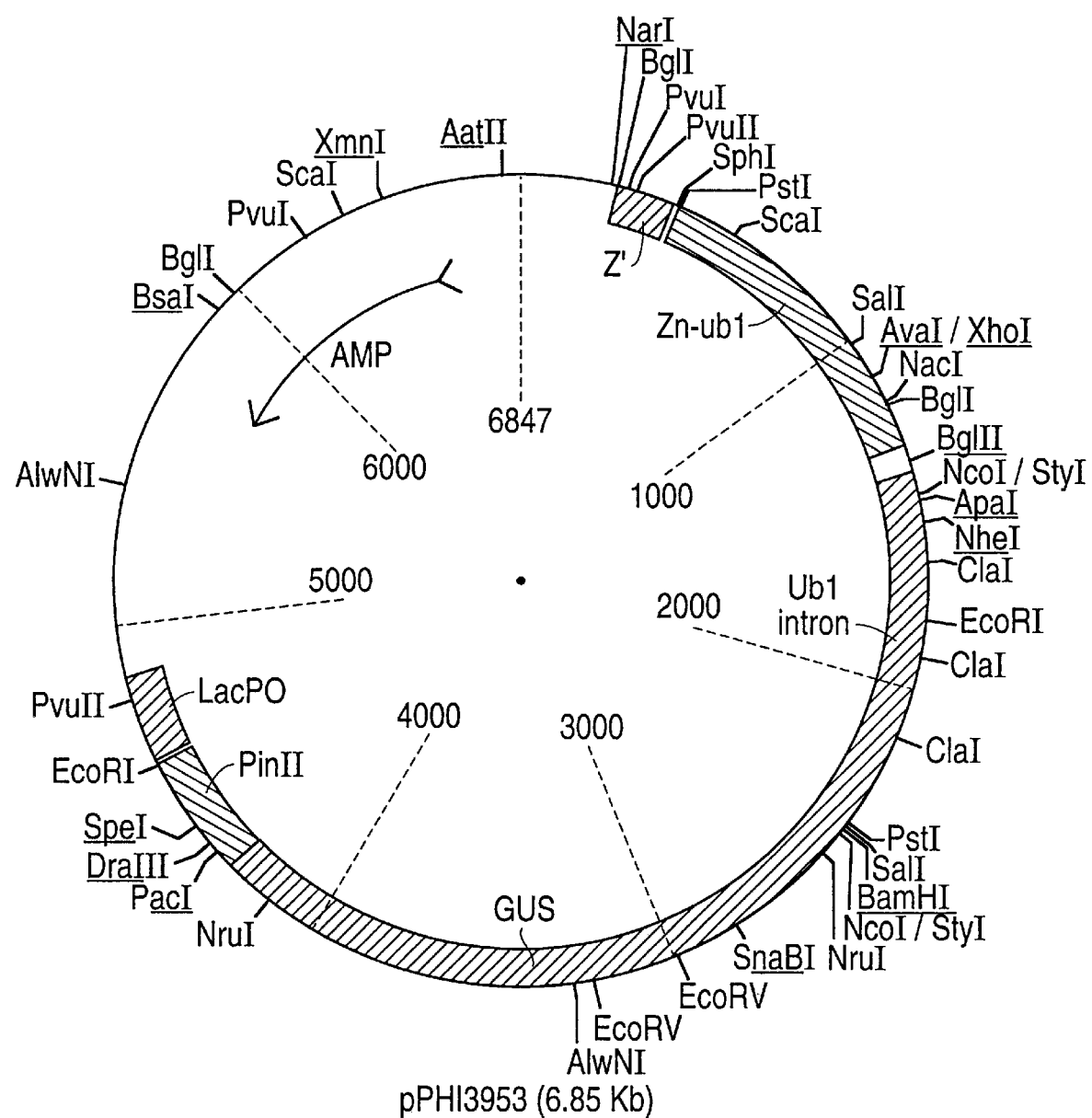
FIG. 1 shows pPHI3953. In pPHI3953 the gus gene is driven by a ubiquitin promoter which includes the first exon and intron, and the gus gene is followed by a PinII transcription termination sequence.

The present inventors have determined that commercial production of GUS in plants is feasible and offers substantial advantages over the conventional approach of obtaining the protein from *E. coli*. The commercial advantage to expressing GUS in plants is primarily a reflection of the greater flexibility of storage of the raw materials. The GUS protein in corn seed was found to be stable when the seed was stored for extended periods. In contrast, *E. coli* fermentation broths would have to be immediately processed; the enzyme is not stable for long periods in the fermentation broth. Whatever storing is employed during *E. coli* production of GUS requires refrigeration of large volumes. This greater flexibility of storing plant tissue which contains GUS translates into significant savings.

In accordance with the present invention, therefore, a DNA molecule comprising a transformation/expression vector is engineered to incorporate GUS-encoding DNA. Extant knowledge concerning the sequence of the uidA gene of *E. coli* permits the isolation and cloning of the gene by standard methodology. As described above, the gene has been cloned, and derivatives optimized for expression in plant have been reported. Therefore, a gus gene for use in the present invention can be subcloned in a vector of choice. For either approach, that is either isolation of the gus gene from the genome, or its subcloning, the methodologies used would include identification of the gene by hybridization with probes, PCR, probe/primer/synthetic gene synthesis, sequencing, molecular cloning and other techniques which are well-known to those skilled in molecular biology.

In a preferred embodiment the gus gene is derived from pRAJ275. See Jefferson et al., *EMBO J.* 6: 3901–07 (1987). The gus gene located on pRAJ275 is a version of the gus gene modified to reflect preferred codon usage in plants. In another preferred embodiment, the gene is synthesized to reflect preferred codon usage in plants. See Murray et al., *Nucleic Acid Res.* 17: 477–498 (1989).

The expression level of GUS can be increased, according to the present invention, by providing the genetic construct containing the gus gene with a sequence encoding a peptide export signal sequence. Thus, the construct is made such that it results in a signal peptide fused to the N-terminal of the GUS mature protein sequence, allowing for normal cellular processing to cleave the protein molecule accurately to yield mature active GUS. Exemplary of suitable peptide export signal sequences is the barley alpha amylase signal sequence. See Rogers, *J. Biol. Chem.* 260: 3731–3738 (1985).

The expression levels of GUS also can be increased by providing the genetic construct containing the gus gene with an intron sequence. In one preferred embodiment, the intron sequence added 5' of the gus gene in effect is the sequence of the first exon and first intron of plant ubiquitin gene. See Cornejo et al. supra.

The methods available for putting together such a relatively short synthetic gene comprising the various modifications for enhancing the expression level described above—intron, peptide export signal sequence, codon usage—can differ in detail. But the methods generally include the designing and synthesis of overlapping, complementary synthetic oligonucleotides which are annealed and ligated together to yield a gene with convenient restriction sites for cloning. The methods involved are standard methods for a molecular biologist.

Once an gus gene has been isolated and engineered to contain some or all features described above, it is placed into an expression vector by standard methods. The selection of an appropriate expression vector will depend upon the method of introducing the expression vector into host cells. A typical expression vector contains: prokaryotic DNA elements coding for a bacterial replication origin and an antibiotic resistance gene to provide for the growth and selection of the expression vector in the bacterial host; a cloning site for insertion of an exogenous DNA sequence, which in this context would code for GUS; eukaryotic DNA elements that control initiation of transcription of the exogenous gene, such as a promoter; and DNA elements that control the processing of transcripts, such as a transcription termination/polyadenylation sequence. It also can contain such sequences as are needed for the eventual integration of the vector into the chromosome.

In a preferred embodiment, the expression vector also contains a gene that codes for a selection marker which is functionally linked to promoters that control transcription initiation. For a general description of plant expression vectors and reporter genes, see Gruber et al., "Vectors for Plant Transformation," in METHODS IN PLANT MOLECULAR BIOLOGY AND BIOTECHNOLOGY 89–119 (CRC Press, 1993).

A promoter element employed to control expression of gus and the reporter gene, respectively, can be any plant-compatible promoter. Those can be plant gene promoters, such as the promoter for the small subunit of ribulose-1,5-bis-phosphate carboxylase, or promoters from tumor-inducing plasmids of *Agrobacterium tumefaciens*, like that nopaline synthase and octopine synthase promoters, or viral promoters such as the cauliflower mosaic virus (CaMV) 19S and 35S promoters or the figwort mosaic virus 35S promoter. See international application WO 91/19806, for example, for a review of known plant promoters which are suitable for use in the present invention.

In a preferred embodiment, the promoter that controls expression of GUS is "tissue-preferred" in the sense that the avidin expression driven by the promoter is particularly high in the tissue from which extraction of the protein is desired; some expression may occur in other parts of the plant. Examples of known tissue-preferred promoters include the tuber-directed class I patatin promoter, Bevan et al., *Nucleic Acids Res.* 14: 4625–38 (1986); the promoters associated with potato tuber ADPGPP genes, Muller et al., *Mol. Gen. Genet.* 224: 136–46 (1990); the soybean promoter of β-conglycinin, also known as the 7S protein, which drives seed-directed transcription, Bray, *Planta* 172: 364–370 (1987); and seed-directed promoters from the zein genes of maize endosperm, Pedersen et al., *Cell* 29: 1015–26 (1982).

In yet another preferred embodiment of the present invention, the exogenous, GUS-encoding DNA is under the transcriptional control of a plant ubiquitin promoter. Plant ubiquitin promoters are well known in the art, as evidenced by European patent application No. 0 342 926. In another preferred embodiment, the selective gene is bar under the transcriptional control of the CaMV 35S promoter. In this construct, transcriptional activity is enhanced by a DNA fragment representing part of the CaMV 35S promoter being placed in a direct repeat tandem arrangement with the CaMV 35S promoter. See Kay et al. (1987), supra. The bar gene confers resistance to bialophos and to tabtoxin-β-lactam toxins. See Gordon-Kamm et al., *The Plant Cell* 2: 603 (1990); Uchimiya et al., *Biotechnology* 11: 835 (1993), and Anzai, et al., *Mol. Gen.* 219: 492 (1989).

In yet another preferred embodiment, separate expression vectors are constructed which contain a gus gene under the control of ubiquitin promoter and the bar gene under the control of the CaMV 35S promoter, respectively. Those vectors then are co-transformed in a plant cell or tissue, as discussed in greater detail below. In another preferred embodiment, both the gus and the bar gene, along with their transcriptional control elements, are located on one DNA molecule.

In accordance with the present invention, a transgenic plant is produced that contains a DNA molecule, comprised of elements as described above, which is integrated into its genome so that the plant expresses a heterologous, GUS-encoding DNA sequence. In order to create such a transgenic plant, the expression vectors containing a gus gene can be introduced into protoplasts; into intact tissues, such as immature embryos and meristems; into callus cultures or into isolated cells. Preferably, expression vectors are introduced into intact tissues. General methods of culturing plant tissues are provided, for example, by Miki et al., "Procedures for Introducing Foreign DNA into Plants," in METHODS IN PLANT MOLECULAR BIOLOGY AND BIOTECHNOLOGY 67–88 (CRC Press 1993), and by Phillips et al., "Cell/Tissue Culture and In Vitro Manipulation," in CORN AND CORN IMPROVEMENT 345–87 (American Society of Agronomy 1988). The reporter gene which is located on the DNA molecule allows for selection of transformants.

Methods for introducing expression vectors into plant tissue include the direct infection or cocultivation of plant tissue with *Agrobacterium tumefaciens*. Horsch et al., *Science* 227: 1229 (1985). Preferably, a disarmed Ti-plasmid is used as a vector for foreign DNA sequences. Transformation can be performed using procedures described, for example, in European applications No. 116 718 and No. 270 822.

Other types of vectors can be used for transforming plant cells by procedures such as direct gene transfer, as described, for example, in PCT application WO 85/01856 and in European application No. 0 275 069; in vitro protoplast transformation, which is the subject of U.S. Pat. No. 4,684,611, for instance; plant virus-mediated transformation, illustrated in European application No. 0 67 553 and U.S. Pat. No. 4,407,956; and liposome-mediated transformation according to U.S. Pat. No. 4,536,475, among other disclosures. Standard methods for the transformation of rice are described by Christou et al., *Trends in Biotechnology* 10: 239 (1992), and by Lee et al., *Proc. Nat'l Acad. Sci. USA* 88: 6389 (1991). Wheat can be transformed by techniques similar to those employed for transforming corn or rice. Furthermore, Casas et al., *Proc. Nat'l Acad. Sci. USA* 90: 11212 (1993), describe a method for transforming sorghum, while Wan et al., *Plant Physiol.* 104: 37 (1994), teach a method for transforming barley. In a preferred embodiment, the transgenic plant of the present invention is maize. Suitable methods for corn transformation are provided by Fromm et al., *Bio/Technology* 8: 833 (1990), and by Gordon-Kamm et al., supra.

In general, direct transfer methods are preferred for the transformation of a monocotyledonous plant, particularly a cereal such as rice, corn, sorghum, barley or wheat. Suitable direct transfer methods include microprojectile-mediated delivery, DNA injection, electroporation, and the like. See, for example, Gruber et al., "Vectors for Plant Transformation," in METHODS IN PLANT MOLECULAR BIOLOGY AND BIOTECHNOLOGY (CRC Press 1993); Miki et al., "Procedures for Introducing Foreign DNA into Plants," loc. cit.; and Klein et al., *Bio/Technology* 10: 268 (1992).

Seed from two independently derived plants, 106155 and 106202, have been deposited with the American Type Culture Collection (ATCC) in Rockville, Md., under Accession Nos. 97330 and 97329, respectively. The two plants are derived from transformation events with two vectors each, comprising elements according to the present invention. The vectors in question are designated pPHI3953 and pPHI3528. The former vector comprises the ubiquitin promoter, including the first exon and intron; a GUS-encoding sequence modified to reflect plant-preferred codon usage; and PinII as a transcription termination sequence. The later vector, comprises a CaMV promoter operably linked to the bar gene.

Optimizing the level of GUS expression is a preferred course of action in implementing the present invention. To this end, it is useful to ascertain expression levels in constructs, transformed plant cells, transgenic plants, and tissue specificity expression, respectively, their levels of GUS expression. There are two assays that can be employed to determine expression levels in this regard. One is a histochemical staining; the other is an enzymatic assay which can be measured spectrophotometrically. Both histochemical and fluorogenic assay methods and protocols for evaluating GUS activity in plant tissues and extracts are well documented in the literature, for example, Jefferson, *Plant Mol. Biol.*, 5: 387–405 (1987) and Klein et al., *Bio/Technology* 6: 559–563 (1988). Enzyme activity units denote nmol of methyl-umbelliferone produced by the GUS-mediated cleavage of methyl-umbelliferone β-glucuronidesubstrate, per mg of total soluble extracted protein, per hour, at 37° C.

The levels of expression of the gene of interest can be enhanced by the stable maintenance of the gus gene on a chromosome of the transgenic plant. Use of linked genes, with herbicide resistance in physical proximity to the gus gene, would allow for maintaining selective pressure on the transgenic plant population and for those plants where the genes of interest are not lost.

With transgenic plants according to the present invention, GUS can be produced in commercial quantities. Thus, the selection and propagation techniques described above yield a plurality of transgenic plants which are harvested in a conventional manner, and GUS then is extracted from a tissue of interest or from total biomass. GUS extraction from biomass can be accomplished by known methods.

It should be evident that, in any extraction methodology, there are inherent loses. In addition there are costs to be considered. Accordingly, a minimum level of expression of GUS is required for the process to be deemed economically worthwhile. The terms "commercial" and "commercial quantities" here denote a level of expression where at least 0.1% of the total extracted protein is GUS. Higher levels of GUS expression would make this undertaking yet more desirable.

According to a preferred embodiment, the transgenic plant provided for commercial production of GUS is maize. In another preferred embodiment, the biomass of interest is seed.

For the relatively small number of transgenic plants that show higher levels of expression, a genetic map can be generated, primarily via conventional RFLP and PCR analysis, which identified the approximate chromosomal location of the integrated DNA molecule. For exemplary methodologies in this regard, see Glick and Thompson in METHODS IN PLANT MOLECULAR BIOLOGY AND BIOTECHNOLOGY 269–84 (CRC Press, 1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR and sequencing, all of which are conventional techniques.

As discussed above, the location on the chromosome of an integrated, GUS-encoding DNA sequence can explain variation in the level of GUS expression obtainable with plants produced according to the present invention. Genetic mapping can be effected, first to identify DNA fragments which contain the integrated DNA and then to locate the integration site more precisely. This further analysis would consist primarily of DNA hybridizations, subcloning, and sequencing. The information thus obtained would allow for the cloning of a corresponding DNA fragment from a plant not engineered with a heterologous gus gene. (In this context, "corresponding" denotes a DNA fragment that hybridizes under stringent conditions to the fragment containing the gus gene.) The cloned fragment can be used for high level expression of another gene of interest. This is accomplished by introducing the other gene into the plant chromosome, at a position and in an orientation corresponding to that of the heterologous gus gene. The insertion site for the gene of interest would not have to be precisely the same as that of the gus gene, but simply in near proximity. Integration of an expression vector constructed as described above, into the plant chromosome then would be accomplished via recombination between the cloned plant DNA fragment and the chromosome. Recombinants where the gene of interest resides on the chromosome in a position corresponding to that of the highly expressed gus gene likewise should express the gene at high levels.

EXAMPLE 1

Construction of an expression vector containing the gus and bar genes

The gus gene was derived from pRAJ275, see Jefferson et al., *EMBO J.* 6: 3901–3907 (1987), and, through a series of intermediate plasmids, was placed downstream of a DNA fragment which was derived from pAHC18 and which contained the maize ubiquitin promoter and the first exon and intron. See Bruce et al., *Proc. Nat'l Acad. Sci. USA* 86: 9692–96 (1989). The final construct is designated pPHI3953—see FIG. 1.

EXAMPLE 2

Generation of gus-expressing, transgenic plants

Immature embryos of Hi-II were used as source tissue for particle bombardment-mediated transformation using a helium powered particle acceleration device (P DS 1000, Bio-Rad). The procedure outlined by Gorden-Kamm, et al., supra was used for transformation and to select plants resistant to bialaphos. Plants initially regenerated from selected embryogenic tissue are termed $T_0$. Subsequent generations are termed T1, T2, etc. Transgenic plants were either selfed or used as females in crosses with untransformed maize plants.

Samples of developing $T_1$ caryopses, 10–30 DAP, and mature seed were bisected and one seed-half was assayed by GUS histochemical reaction with the remaining halved embryo and endosperm assayed quantitatively for GUS by methods discussed in the specifications.

EXAMPLE 3

GUS extraction and analysis

Table 1 is a compilation of the biochemical characteristics of the GUS derived from corn, relative to commercially available GUS obtained from Sigma Chemical Company, St. Louis, Mo. It is evident that the GUS from the two sources were biochemically similar. This conclusion is further supported by partial N-terminal sequencing of the two proteins, which indicates that GUS from the two sources contained an identical amino acid (aa) sequence (see Table 2) (SEQ ID NOS:1–2, respectively). The quantitative results of extraction of GUS from corn seed indicated that upwards of 0.5% total extracted protein was functional GUS enzyme.

The results presented in Table 1 and Table 2 were obtained as follows. The molecular weight was determined by gel electrophoresis, on 4–20% SDS-polyacrylamide gels from Novex, San Diego, Calif. GUS from the two sources was run in parallel with protein molecular weight standards from Novex. The Km of both enzymes were determined by the enzyme assay described by Jefferson, *Plant Molec. Biol.* 5: 387–405 (1987). This flourometric assay measures the cleavage of 4-methylumbelliferyl glucuronide to methylumbelliferone. Determination of the isoelectric point for both proteins was performed using a Novex IEF gel system (San Diego, Calif.). General methods of determining the isoelectric point of proteins are provided by Walker, "Isoelectric Focusing of Proteins in Ultra-Thin Polyacrylamide Gels," in 32 METHODS IN MOLECULAR BIOLOGY 59–65 (Humana Press 1994). Both GUS from corn and from Sigma were shown to be stable at 50° C. for 30 minutes via the assay described by Jefferson (1987), supra. GUS from both sources was also determined to be antigenically similar by western blot analysis using affinity-purified polyclonal antibodies against GUS. Tobwin et al., *Pro. Nat'l Acad. Sci. USA* 76: 4350–54 (1979). General methods for N-terminal sequencing of proteins are provided by Charbonneau, "Strategies for Obtaining Partial Amino Acid Sequence Data from Small Quantities of Pure or Partially Purified Protein," in A PRACTICAL GUIDE TO PROTEIN AND PEPTIDE PURIFICATION FOR MICROSEQUENCING 15–30 (Academic Press 1989).

TABLE 1

BIOCHEMICAL CHARACTERIZATION OF GUS

|  | GUS FROM SIGMA | GUS FROM CORN |
|---|---|---|
| Molecular Weight | 68,000 | 68,000 |
| Km | 0.21+/−0.04 (nM) | 0.19+/−0.05 (nM) |
| pI | 4.8 to 5.0 | 4.8 to 5.0 |
| Heat Stable | Yes | Yes |
| Antigenic Similarity | Yes | Yes |

TABLE 2

N-TERMINAL PROTEIN SEQUENCING DATA

|  | GUS FROM SIGMA | GUS FROM CORN |
|---|---|---|
| 1 | Met |  |
| 2 | Leu | Val |
| 3 | Arg | Arg |
| 4 | Pro | Pro |
| 5 | Val | Val |
| 6 | Glu | Glu |
| 7 | Thr | Thr |
| 8 | Pro | Pro |

What is claimed is:

1. A method of producing B-glucuronidase (GUS) in commercial quantities comprising the steps of (i) providing biomass from a plurality of plants, wherein at least some plants of said plurality express a DNA molecule comprised of (A) a heterologous nucleotide sequence coding for GUS and (B) a promoter operably linked to said nucleotide sequence to effect expression of GUS; and (ii) extracting GUS from said biomass wherein at least 0.1% of total extracted protein is GUS.

2. A method according to claim 1, wherein said biomass is comprised of seeds.

3. A method according to claim 1, wherein about 0.5% of total extracted protein in said biomass is GUS.

4. A method according to claim 3, wherein said biomass is comprised of seed.

5. A transgenic plant produced by a process comprising the steps of:

(a) providing cell or regenerable plant tissue that contains (i) a plant-compatible promoter, (ii) a signal sequence and (iii) a heterologous, GUS-encoding DNA sequence, wherein elements (i)–(iii) are operably linked, (b) propagating a plurality of transgenic plants from said cell or said plant tissue, and then (c) identifying from among said plurality a transgenic plant that expresses GUS such that at least 0.1% of total extracted protein is GUS.

6. A transgenic plant according to claim 5, wherein said heterologous nucleotide sequence encoding GUS incorporates plant-preferred codons.

7. A transgenic plant according to claim 5, wherein said DNA molecule further comprises an intron sequence or a peptide export signal sequence which modifies expression of said heterologous nucleotide sequence.

8. A transgenic plant according to claim 7, wherein said DNA molecule comprises said intron sequence.

9. A transgenic plant according to claim 7, wherein said DNA molecule comprises said peptide export signal sequence.

10. A transgenic plant according to claim 5, wherein said plant is a corn plant.

11. A transgenic plant according to claim 5, wherein said plant is strain 106155 and seeds of said strain are deposited under ATCC accession no. 97330.

12. A transgenic plant according to claim 5, wherein said plant is strain 106202 and seeds of said strain are deposited under ATCC accession no. 97329.

13. A transgenic plant according to claim 5, wherein about 0.5% of said total extracted protein is GUS.

14. A transgenic plant according to claim 5, wherein said promoter is the ubiquitin promoter.

15. A transgenic plant according to claim 5, wherein said promoter is a tissue-preferred promoter.

16. A transgenic plant according to claim 8, wherein said intron sequence is a plant ubiquitin intron sequence.

17. A transgenic plant according to claim 16, wherein said DNA molecule further comprises part of ubiquitin gene first exon.

18. A transgenic plant according to claim 9, wherein said peptide export signal sequence is a barley alpha amylase peptide export signal sequence.

19. Seed that is the product of a plant according to claim 5.

20. Seed that is the product of a plant according to claim 13.

* * * * *